United States Patent
Chung et al.

(10) Patent No.: US 7,928,740 B2
(45) Date of Patent: Apr. 19, 2011

(54) METHOD FOR POSITIONING CARBON NANOTUBES BETWEEN ELECTRODES, BIOMOLECULE DETECTOR BASED ON CARBON NANOTUBE-PROBE COMPLEXES AND DETECTION METHOD USING THE SAME

(75) Inventors: Won Seok Chung, Hwaseong-si (KR); Kyu Tae Yoo, Seongnam-si (KR); Jeo Young Shim, Yongin-si (KR); Junghoon Lee, Seongnam-si (KR); Misun Cha, Seoul (KR); JungIm Han, Yongin-si (KR); Seungwon Jung, Seou-gu (KR)

(73) Assignees: Samsung Electronics Co., Ltd. (KR); Seoul National University Industry Foundation (KR)

( * ) Notice: Subject to any disclaimer, the term of this patent is extended or adjusted under 35 U.S.C. 154(b) by 795 days.

(21) Appl. No.: 11/939,969

(22) Filed: Nov. 14, 2007

(65) Prior Publication Data

US 2010/0289509 A1  Nov. 18, 2010

(30) Foreign Application Priority Data

May 15, 2007 (KR) .......................... 10-2007-0047239
Sep. 28, 2007 (KR) .......................... 10-2007-0098352

(51) Int. Cl.
*G01R 27/08* (2006.01)

(52) U.S. Cl. ....................................... 324/692; 977/852
(58) Field of Classification Search .................. 324/692, 324/691, 649, 600; 977/840, 842, 852, 858, 977/872, 880
See application file for complete search history.

(56) References Cited

U.S. PATENT DOCUMENTS

| | | | |
|---|---|---|---|
| 4,681,840 A * | 7/1987 | Stephenson et al. | 435/6 |
| 7,381,316 B1 * | 6/2008 | Lee et al. | 204/483 |
| 7,491,428 B2 * | 2/2009 | Smits et al. | 427/458 |
| 2007/0231988 A1 * | 10/2007 | Yoo et al. | 438/199 |
| 2007/0268739 A1 * | 11/2007 | Yoo et al. | 365/151 |
| 2009/0173527 A1 * | 7/2009 | Benke et al. | 174/261 |
| 2009/0208922 A1 * | 8/2009 | Choi et al. | 435/4 |
| 2009/0321261 A1 * | 12/2009 | Vlahovic et al. | 204/545 |

OTHER PUBLICATIONS

"Composite Electric-field Guided Assembly of Single Walled Carbon Nanotube and Functionalization by Single Stranded DNA" (Dec. 2005).

* cited by examiner

*Primary Examiner* — Hoai-An D Nguyen
(74) *Attorney, Agent, or Firm* — Cantor Colburn LLP

(57) ABSTRACT

A device and method are disclosed for detecting biomolecules. More specifically, by measuring the change in the electrical properties of a complex between a probe and carbon nanotubes, a non-label detection is achieved, capable of a rapid, sensitive and electrical detection of the presence and concentration of biomolecules in a sample solution.

25 Claims, 11 Drawing Sheets

Double layer on Si substrate nanoimprint

Oxygen plasma etching

Metallization & lift off

After nanoimprint

After oxygen plasma etching

After metallization & lift off

US 7,928,740 B2

METHOD FOR POSITIONING CARBON NANOTUBES BETWEEN ELECTRODES, BIOMOLECULE DETECTOR BASED ON CARBON NANOTUBE-PROBE COMPLEXES AND DETECTION METHOD USING THE SAME

CROSS-REFERENCES TO RELATED APPLICATIONS

The present invention claims priorities of Korean patent application No. 10-2007-0047239 filed on May 15, 2007, and Korean patent application No. 10-2007-0098352 filed on Sep. 28, 2007, which are hereby incorporated by reference in their entirety.

BACKGROUND OF THE INVENTION

1. Field of the Invention

The present invention relates to a method and device for electrically detecting biomolecules.

2. Description of the Prior Art

Carbon nanotubes (CNTs) have a tremendous potential for a wide variety of applications due to their unique mechanical, electrical, and chemical characteristics. The CNTs have excellent characteristics such as extremely high electrical conductivity, high length-to-diameter ratio, and excellent structural strength. Thus, it is expected that CNTs can be used to produce new products that have unique properties compared with existing ones.

Single-walled carbon nanotubes (SWCNTs) have attracted attention as new nano-biosensor materials because of their high aspect ratios, excellent chemical, mechanical, and electrical characteristics. SWCNTs exhibit a pronounced change in their electrical characteristics even when reacted to a trace amount of biomolecules. Thus, SWCNT biosensors have been developed that can detect the change in the characteristics of the SWCNTs before and after the reaction to the biomolecules. In the case of most of the presently available biosensors using the SWCNTs, attempts have been made to detect biomolecules with field effect transistors (FETs) or Schottky barrier transistors. These methods generally have difficulties in immobilizing the probe on the surface of the SWCNTs, and are subjected to bonding between the SWCNTs and the biomolecules since the reaction occurs on the surface of a substrate. This bonding is inefficient, since the biomolecule has to be bonded to the SWCNT.

Further, there still exists a possibility of alteration in the characteristics of the SWCNT or the target biomolecules due to immobilization of the SWCNT on the surface of the biosensor, or immobilization of the target biomolecules on the surface of the SWCNT.

In cases where a non-electrical method is used to detect the biomolecules, fluorescent or other chemical labels are usually attached to the targets to be detected, and then signals generated from the labels are measured. In this case, a pre-treatment process such as labeling target samples is most often utilized and these processes are usually time-consuming, so that it is difficult to analyze various samples in a short time. Further, it is difficult to verify that the labels are attached only to the target biomolecules in the process of the labeling.

Thus, it is desirable to have a method and device capable of rapidly and accurately detecting the target biomolecules without any sample pre-treatment process such as the labeling or bonding.

SUMMARY OF THE INVENTION

Disclosed herein is a device for electrical detection of biomolecules comprising a substrate; a pair of electrodes formed on the substrate and having a gap therebetween; an electrode capable of applying a voltage between either one of the pair of electrodes and the substrate; a detection solution comprising carbon nanotube-probe complexes, the probe being capable of interacting with target biomolecules; a means for positioning the carbon nanotube in the detection solution on a gap between the electrodes; and a means for measuring a change in electrical characteristics.

Disclosed herein too is a method for fabricating a device for electrical detection of biomolecules comprising mixing a carbon nanotube with a probe which is a material capable of interacting with target biomolecules in a solution, thereby forming a detection solution that comprises a carbon nanotube-probe complex; contacting the formed detection solution with a sample solution to form a mixture; the sample solution comprising biomolecules to be tested; and positioning the mixture of the detection solution and the sample solution in a gap between electrodes on a substrate; arranging the carbon nanotube-probe complex or the carbon nanotubes in the mixture in the gap between the electrodes, the arranging being accomplished by the application of a composite electric field; the composite electric field comprising an alternate current electric field and a direct current electric field that is in a continuous or non-continuous form.

Disclosed herein too is a method for electrically detecting biomolecules, comprising mixing a carbon nanotube with a probe; the probe being a material that interacts with target biomolecules in a solution; the interaction resulting in the formation of a detection solution that comprises a carbon nanotube-probe complex; contacting the formed detection solution with a sample solution to form a mixture; the sample solution comprising biomolecules to be tested; positioning the mixture of the detection solution and the sample solution in a gap between electrodes on a substrate, thereby arranging the carbon nanotube-probe complex or the carbon nanotubes in the gap between the electrodes; and generating an electric field effect between the electrodes; and, measuring a first electric field effect.

Disclosed herein too is a method of positioning a carbon nanotube or a carbon nanotube-probe complex in a gap between electrodes, comprising disposing a solution comprising the carbon nanotube or the carbon nanotube-probe complex in the gap between the electrodes on a substrate; and arranging the carbon nanotube-probe complex or the carbon nanotube in a gap between the electrodes by applying a composite electric field; the composite electric field comprising an alternate current electric field and a direct current electric field that is in a continuous or non-continuous form.

BRIEF DESCRIPTION OF THE DRAWINGS

The above and other objects, features and advantages of the present invention will be more apparent from the following detailed description taken in conjunction with the accompanying drawings, in which:

FIG. 7 is a graph showing measured electrical characteristics of the reacted SWCNT-ssDNA complexes and the unreacted complexes.

DETAILED DESCRIPTION OF THE EXEMPLARY EMBODIMENTS

Figure 1:
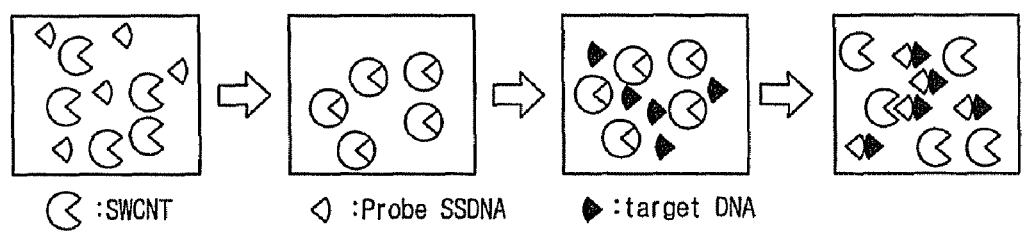
FIG. 1 is a picture showing the principle of the detection method of the present invention in which the target biomolecule is DNA, and the probe is a complementary single-stranded DNA(ssDNA) to the target DNA, wherein an SWCNT-ssDNA complex is formed from a single-walled carbon nanotube (SWCNT) and ssDNA and this complex reacts to target DNA.

Disclosed herein is a device and a method capable of measuring the existence and concentration of the target biomolecules in a simple, rapid, and accurate manner without immobilizing the biomolecules through covalent bonds or labeling the biomolecules with optical or chemical labels. The device and method for biomolecule detection is based on interactions between free carbon nanotubes (CNTs) or a CNT-probe complex and the target biomolecules in a solution without growing or immobilizing the CNTs or the CNT-probe complex on a specific substrate prior to CNT-biomolecule interaction. The device and method can detect a very small quantity of target biomolecules with extremely high sensitivity. More specifically, the method permits the detecting of biomolecules with a high reaction efficiency and sensitivity through reaction between the CNT-probe complexes and the biomolecules and positioning the products of reaction (CNTs or CNT-probe complexes) at desired positions to measure the electrical characteristics of the products of reactions.

Herein, "target biomolecules" refer to all biomolecules that interact with "probes," which will be described below, and are capable of disassembling the complex of the probe and CNT. Thus, all the biomolecules meeting this condition correspond to the target biomolecules, and the scope of these biomolecules are not limited to proteins, nucleic acids, lipids, carbohydrates, or specific complex molecules thereof.

Herein, "probes" refer to all molecules capable of interacting with the CNTs to form complexes. The probe is capable of changing the electrical characteristics of the CNTs when it is assembled with the CNTs to form a complex. Such complexes need not be based on a chemical bond such as a covalent or an ionic bond, and it is sufficient if they have strength enough to maintain the complexes under the measurement conditions for the detecting device. Preferably, when the probes are bonded with the metallic (or conductive) CNTs, the CNT-probe complexes exhibit characteristics of a semiconductor. Furthermore, it is desirable for the probes to be capable of being wholly or partly dissociated from the complexes when an interaction between the probe and the target biomolecules occurs. The probes may include proteins, nucleic acids, lipids, or saccharides that bind with the target protein molecules, or nucleic acid that have complementary sequences to target nucleic acid molecules. Further, the probes may include proteins such as leptin that form strong complexes with specific carbohydrate molecules, or proteins such as hormone receptor proteins that are combined with hormones. However, the probe can make use of any molecule having these characteristics, and thus is not limited only to the biomolecule.

Herein, the "change in electrical characteristics" refers to any change in the electrical characteristics of a CNT-probe complex that arises out of the interaction between the probe and the target biomolecules. For example, changes in electrical characteristics include a change in electrical resistance, or conversion of electrical property between a conductor and a semiconductor.

In one embodiment, an electric field effect is generated in a device that comprises a pair of electrodes functioning as the source and the drain on a substrate and a gate capable of controlling electric current between the source and the drain by applying voltage. A gap between the electrodes ranges from tens of micrometers (μm) to tens of nanometers (nm) and the electric field effect is measured with a proper measuring means. One example of a typical electric field effect device is a field effect transistor (FET).

However, in the electric field effect device of the present disclosure, the CNTs or the CNT-probe complexes act as a channel, through which electric current between the source and the drain flows. For this reason, the electric field effect device is characterized in that it does not have a doped silicon layer serving as the channel for electric current, which is different from ordinary FETs. Thus, the field effect device can be provided by modifying an ordinary FET, or by producing a new one. The electric field effect can be measured, for instance, by measuring the electric current or voltage between the source and the drain.

In one embodiment, the CNTs can be single-walled carbon nanotubes (SWCNTs) or multi-walled carbon nanotubes (MWCNTs) and are preferably SWCNTs. The CNTs used for the detection are preferably metallic (or conductive) nanotubes.

An embodiment of detecting the presence of deoxyribonucleic acid (DNA) in a solution sample using the biomolecule detecting device will now be described in detail. The SWCNT and a single-stranded DNA (ssDNA) form a complex due to the characteristics of their molecular structures. The DNA winds itself around the CNT. However, the overall structure of the complex may be of any other shape. For example, the DNA may be attached to the CNT in parallel position. When the complex contacts with a specific DNA molecule, i.e., the target DNA molecule, complementary to the ssDNA (disposed on the probe), the probe ssDNA is disassembled from the complex and a double-stranded DNA (dsDNA) is formed due to hybridization between the target DNA and the probe DNA (i.e., the DNA disposed on the CNT) (see FIG. 1). However, when the complex contacts a non-specific DNA that is not complementary to the probe DNA, the complex keeps its form without being dissembled. Because the hybridization between DNA and RNA or between RNA and RNA is well-known phenomena, this principle can be generally applied to those cases in which the target biomolecules and the probes are not only DNA but also other nucleic acids.

In an embodiment in which the target biomolecule is DNA and the probe is the ssDNA complementary to the target DNA, it has been discovered that the complex comprising metallic SWCNT and ssDNA has semiconducting characteristics. Thus, the electrical characteristic of the metallic SWCNT differs from that of the SWCNT-ssDNA complex, and this fact makes it possible to detect target DNA, when the target DNA are complementary to the probe DNA in an easy and accurate manner using a device based on measuring an electric field effect, as described below.

1. SWCNTs are mixed with the ssDNAs complementary to the target DNA in the appropriate solution and the SWCNTs and ssDNAs form SWCNT-ssDNA complexes.

2. The sample solution to be tested for the presence of the target DNA is mixed to the solution containing the SWCNT-ssDNA complexes. If the target DNA exists in the sample solution, reaction between target DNAs and ssDNAs in the complexes disassembles the SWCNT-ssDNA complexes into the SWCNTs and the ssDNAs.

3. Resultant products of reaction (the SWCNT-ssDNA complexes or the SWCNTs) processed in step 2, are positioned in the gap between the electrodes of the electric field effect device to measure the electrical characteristics of products of reaction.

4. The electric field effect is measured with a gate voltage sweep applied to the electric field effect device. Then, it can be determined whether the target DNA exists in the sample solution or not from the measured data (metallic or semiconducting characteristics of products of reaction in step 2).

Both the processes of forming the complex and the contacting of the complex with the complementary DNA take place in a solution. In order to measure the electric characteristics of a resultant product of the contacting, it is important to manufacture the proper electrodes and to arrange the products of the contacting, i.e. the SWCNT-ssDNA complexes or SWCNTs, in the gap between the electrodes after the reaction (see FIG. 5).

Figure 2A:
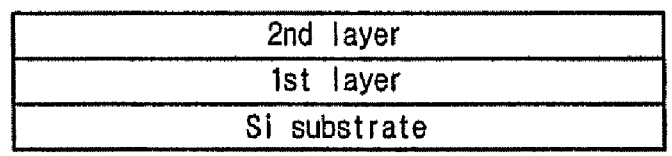
FIG. 2 is a view showing an electrode manufacturing process using nanoimprint lithography (NIL) and resultant electrode with a nano-sized gap.
Figure 2A:
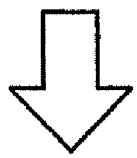
Figure 2A:
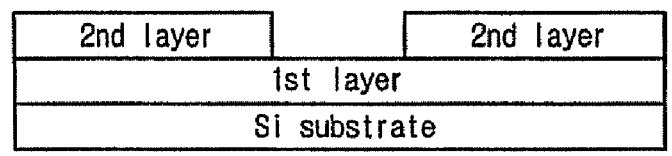
Figure 2A:
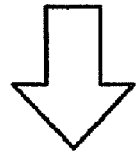
Figure 2A:
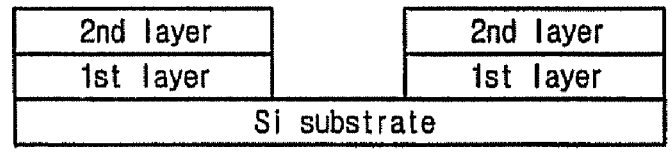
Figure 2A:
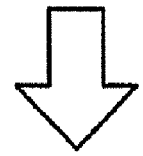
Figure 2A:
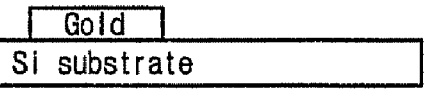
Figure 2B:
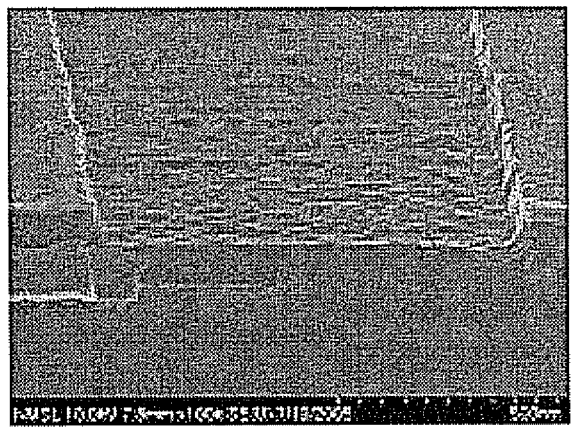
Figure 2B:
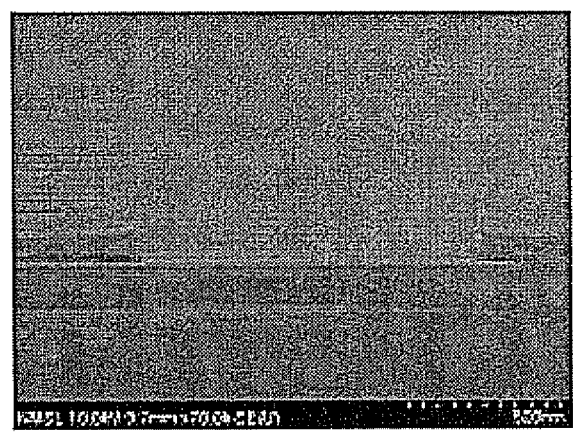
Figure 2B:
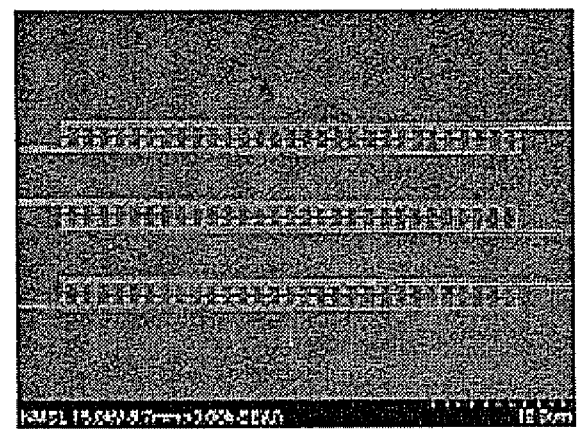

FIG. 2A represents exemplary schematic views of the process of manufacturing the electrode, while FIG. 2B shows micrographs that depict the result at each step in the manufacturing of electrodes having a suitable gap size. FIG. 2A shows the manufacturing of an electrode using nanoimprint lithography (NIL). First, a substrate coated with a polymeric protection layer is pressed in a mold. In the embodiment depicted in the FIG. 2A, the polymeric protection layer comprises a first layer and a second layer. The substrate generally comprises silicon, while the first layer comprises polymer, e.g., PMMA (polymethyl methacrylate) or PMGI (polymethyl glutarimide), and the second layer comprises resin for imprint. The first layer is deposited on the substrate to protect the substrate. The second layer is deposited on the first layer to form a pattern on the first layer. Further, the second layer may protect the first layer as a mask later during the etching process. The first layer and the second layer may be deposited by spin coating. Then, the protection layer is cross-linked using heat or light. The mold is removed and the first and second protection layers on the substrate are removed by oxygen plasma etching. Following the oxygen plasma etching, a metal electrode is disposed upon the substrate. When metal electrodes (e.g., Au in FIG. 2A) are directly deposited on an undoped silicone substrate as in the embodiment shown in FIGS. 2A and 2B, there is no a channel for electric current between the electrodes functioning as a source and a drain. In one embodiment, it may not be desirable to remove the insulating layer laminated on the substrate. The metal electrodes can be directly disposed on a doped polymeric layer. Following the deposition of the electrodes, the CNTS or the CNT-probe complexes are arranged on a gap between the electrodes to function as a channel. However, it is not essential to use the undoped silicone substrate, but various materials including doped silicone and other synthetic resins can be used for the substrate.

It is desirable to arrange the CNT-probe complexes or the CNTS on a gap between the electrodes. This is generally accomplished using dielectrophoresis (DEP) with only an alternating current (AC).

Figure 3:
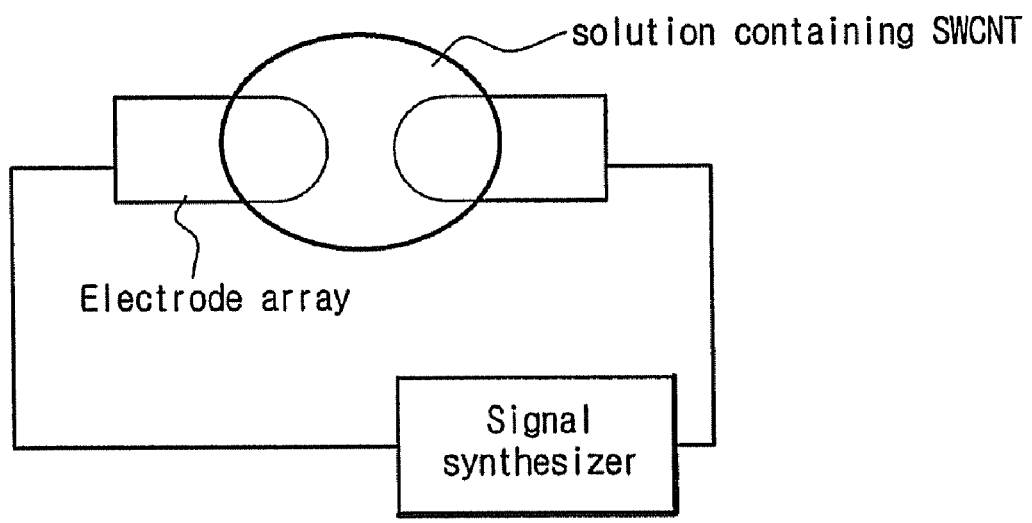
FIG. 3 is a schematic view of a device for positioning SWCNT on the electrodes with a nano-sized gap using a composite electric field guided assembly.

In another embodiment, composite electric field-guided assembly (CEGA) is used to arrange the CNT-probe complexes or the CNTS on the gap between the electrodes. This is accomplished as follows: a solution containing the dispersed CNTs is placed on a gap between pre-patterned electrodes and then a composite electric field with a specific condition is applied to the solution through the electrodes for the purpose of arranging the CNTs as intended (see FIG. 3). Applying the composite electric field means that both of AC and DC electric fields are applied to the electrodes simultaneously. The DC electric field may be a typical electric field or a pulsed electric field. Hereinafter the pulsed electric field will be referred to as a "pseudo-DC electric field." By properly selecting the intensity and the frequency of the AC and DC electric fields of the composite electric field, orienting of the CNTS or CNT-probes between the electrodes can be achieved.

The CEGA has advantages when compared to existing methods in the following aspects:

1) Since the CNT or the CNT-probes are assembled by forcibly orienting them (while disposed in a solution) to an electrode, it is advantageous to detect a CNTs or CNT-probes when present in a low density, when used in a measurement. Consequently, it is possible to automatically assemble one nano element in a desired position.

2) The CNTs can be assembled selectively. When conductive CNTs are mixed with semi-conducting CNTs, the conducting or semi-conducting CNTs can be selectively located and assembled only by adjusting the frequency and the voltage.

3) Electro-osmotic force by AC current acts to straighten the CNTs as well as generate a downstream flow so that the CNTs can be more easily attached to the electrodes. When an electric field is applied on both of the electrodes, the solution positioned in the gap between the electrodes is forced and forms a current therewithin towards the substrate (i.e., perpendicular to the substrate). The downstream flow means such flow of the solution in the gap between the electrodes when the electric field is applied to the electrodes.

Figure 8A:
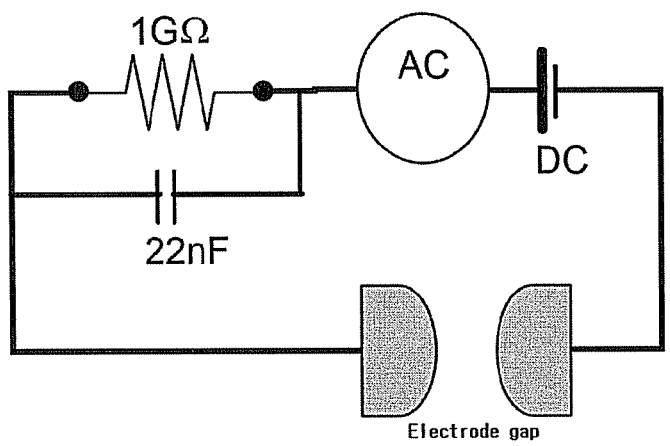
FIG. 8A is a circuit diagram illustrating an example of composite electric field-guided assembly device.
Figure 8B:
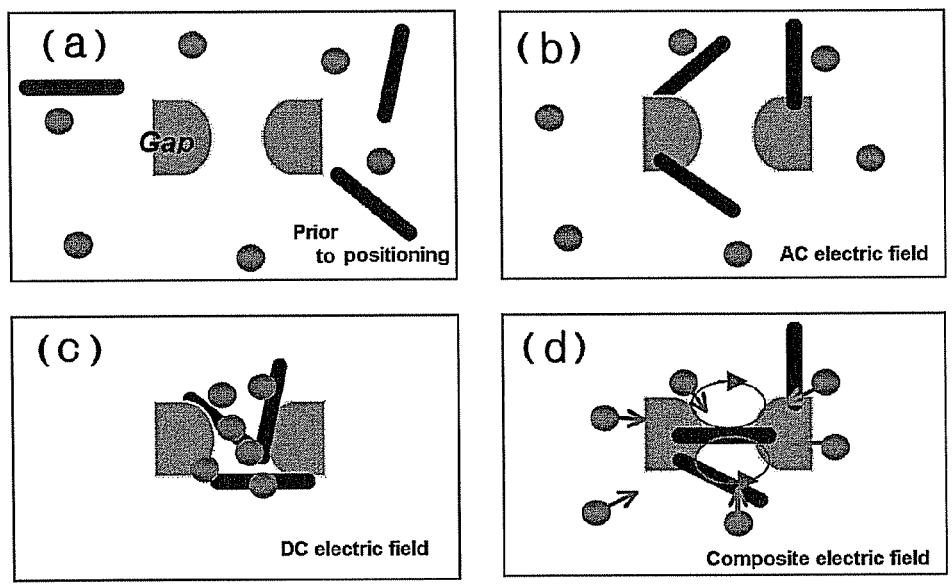
FIG. 8B shows the effect of the different electric fields (composite, AC only and DC only) upon the arrangement and the assembly of the CNTs.

FIG. 8A is a circuit diagram illustrating an example of an apparatus for applying such a composite electric field. According to the circuit shown in FIG. 8A, DC and AC power sources are connected in series and a capacitor and a resistor having a high resistance value are connected in parallel. FIG. 8B is a conceptual view illustrating a process of positioning CNTs on a gap between pair of electrodes using the device as shown in FIG. 8A. In FIG. 8B, (a) indicates a situation prior to the application of a composite electric field, the rods in the figure representing CNTs, while the dots represent other impurities (b) indicates a situation where dielectrophoresis takes place only by an AC electric field, (c) indicates a situation where dielectrophoresis takes place only by a DC electric field, and (d) the CNTs are assembled by a composite electric field.

The DC electric field may be implemented in the form of a pseudo-DC electric field as mentioned above. This is effective in a case where biomolecules to be detected are suspended or dissolved into a buffer solution, where inorganic and organic salts are dissolved, for the purpose of stability and functionality of the biomolecules. In the case of applying an ordinary continuous DC electric field in order to arrange the CNTs included in a buffer solution, where salts are dissolved, electrodes can be damaged due to electrolysis. In this case, using a pulsed, pseudo DC electric field makes it possible to arrange the CNTs between the pair of electrodes without damaging the electrodes.

Figure 5:
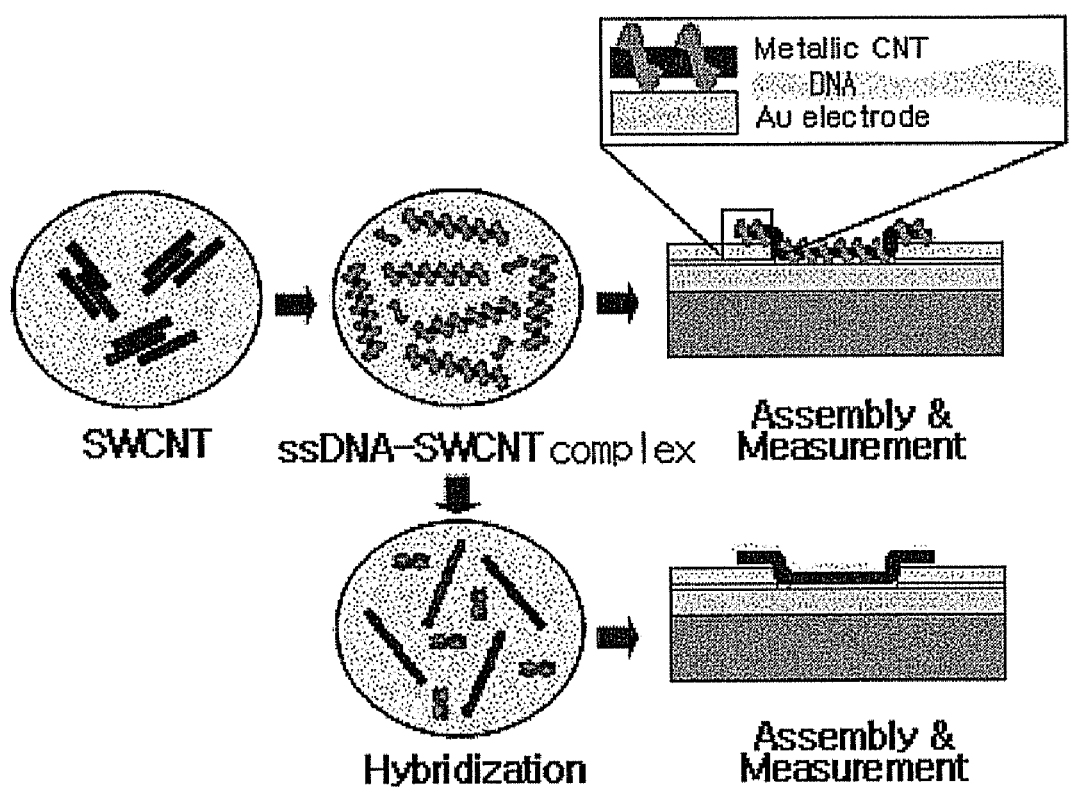
FIG. 5 is a conceptual view showing the procedure for positioning SWCNT-DNA complexes reacted to target DNA in a solution and un-reacted complexes on the electrodes.
Figure 6:
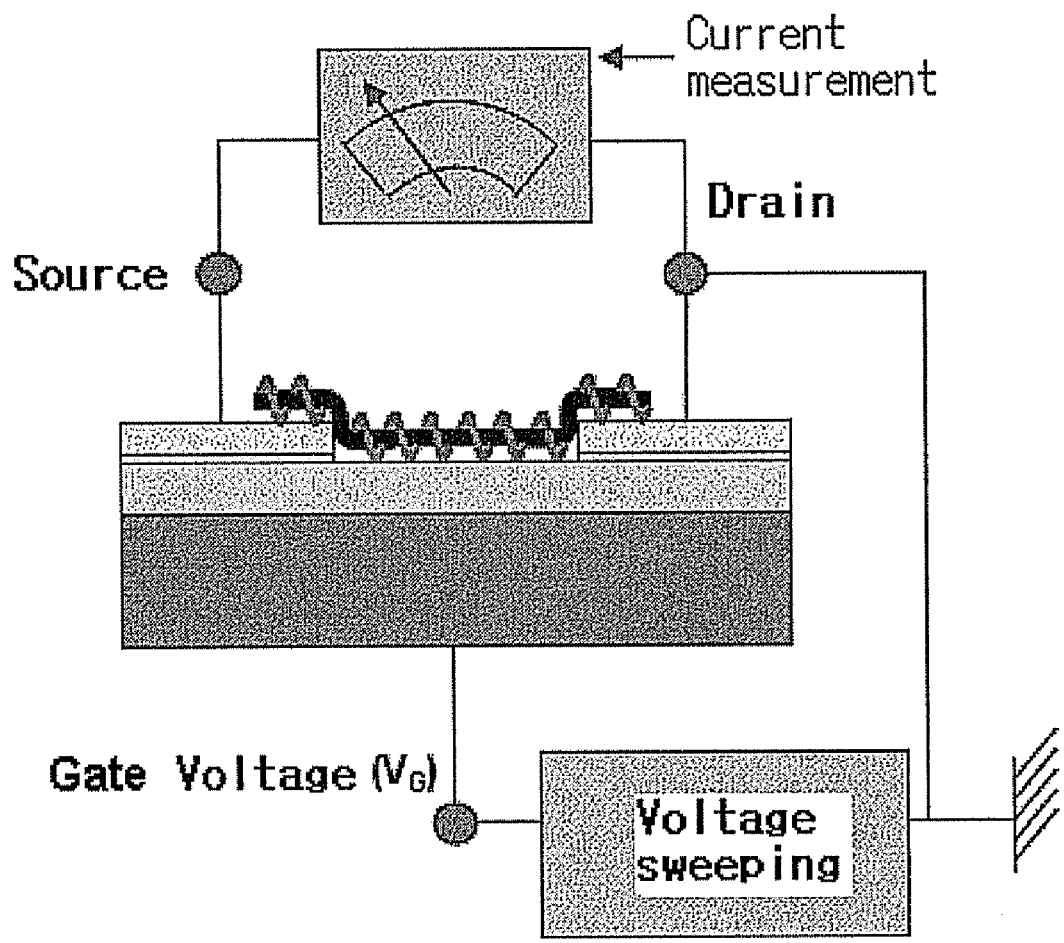
FIG. 6 is a conceptual view of a device for measuring electrical characteristics of SWCNT-ssDNA complex or SWCNT on the electrodes.

After the CNTs or CNT-probe complexes are positioned between the pair of electrodes of a field effect device by the CEGA method or other known methods, field effect is measured (see FIG. 5). This is different from a typical FET in that the CNTs or the CNT-probe complexes act as a channel of current, which flows between a source and a drain (i.e., a pair of electrode). The method of measuring the field effect can be implemented with any method that measures a current flowing between the source and the drain or other known methods that measure the electric characteristics of the FET. A concept of measuring the electric current is illustrated in FIG. 6.

EXAMPLES

Hereinafter the present invention will be described in more detail with reference to Examples. It should be construed that Examples are give for the illustrative purposes only but do not limit the scope of protection of the present invention.

Example 1

Production and Hybridization of SWCNT-ssDNA Complexes

In order to make SWCNT-ssDNA complexes, metallic SWCNTs (available from Carbon Nanotechnologies Inc. in Texas, USA) were sonicated for 90 mins in a DNA solution (15 μm 18-mer Poly (dG) or Poly (dC)), which was dissolved into deionized water, followed by a centrifugation to remove impurities. While the deionized water was used in Example 1, the DNA solution can be implemented with other suitable buffer solutions such as 0.1 M NaCl solution or PBS solution. The average length of the SWCNTs used was about 1 μm.

In order to hybridize a portion of the produced complexes with a target DNA (for example, the target DNA is complementary 18-mer poly (dC) DNA to 18-mer poly (dG) in the case that the probe is 18-mer poly (dG)), the solution containing the complex was added with the same amount of a 15 μm solution of the DNA to be detected. Then, the resultant solution was allowed to react overnight (about 24 hours).

The complexes and the hybridized complexes were used in the field effect measurement.

Example 2

Arranging SWCNT-ssDNA Complexes or SWCNTs in Electrode Gap

By using the CEGA method, the SWCNT-ssDNA complexes formed in Example 1 or the hybridized complexes (i.e., SWCNT with ssDNA dissociated) were located between the electrodes of a field effect device. A circuit as shown in FIG. 8A was used to generate a composite electric field. In the case of arranging the SWCNT-ssDNA complexes or the SWCNTs using the CEGA method, it is difficult to present general arrangement conditions, which can be widely used, since the arrangement of the SWCNT-ssDNA complexes or the SWCNTs is variable according to the gap size of the electrodes, the length of the SWCNTs and reaction conditions.

In Example 2, a device of generating field effect, which has an electrode gap of 300 nm, was manufactured using the aforementioned nanoimprint lithography. In the composite electric field used to position the SWCNT-ssDNA complexes or the SWCNTs produced in Example 1, the frequency of an AC electric field was 5 MHz, the intensity of the AC electric field was 2.96 $V_{peak}$, and an intensity ratio of DC to AC electric field was 0.345.

While an ordinary continuous DC electric field was used instead of the CEGA, it is preferable to use a pulsed pseudo DC electric field where the SWCNT and ssDNAs are dissolved into a buffer solution unlike the water used in Example 1 above.

Figure 4:
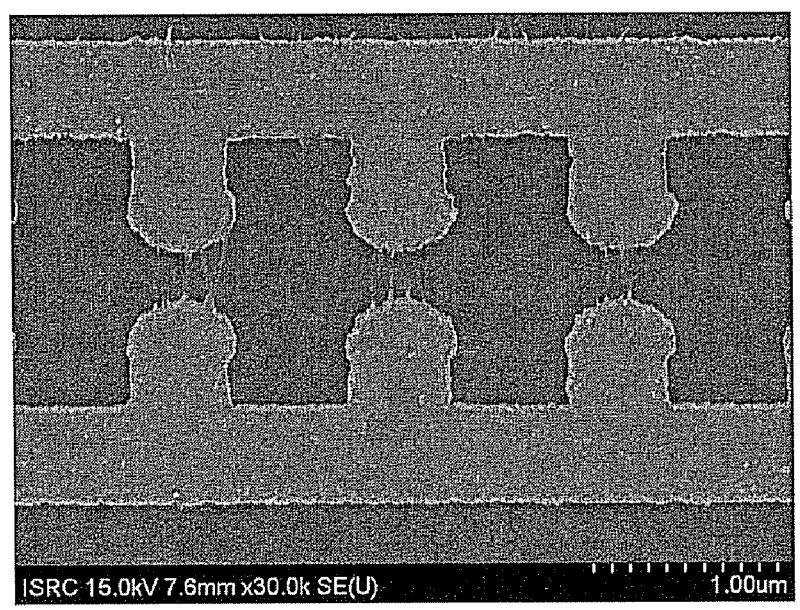
FIG. 4 is a picture showing SWCNT-ssDNA complex positioned on the electrodes with a nano-sized gap.

FIG. 4 is a picture illustrating SWCNT-ssDNA complexes assembled between electrodes having an electrode gap of 300 nm, by using the aforementioned CEGA method.

Example 3

Measuring Field Effect

Figure 7A:
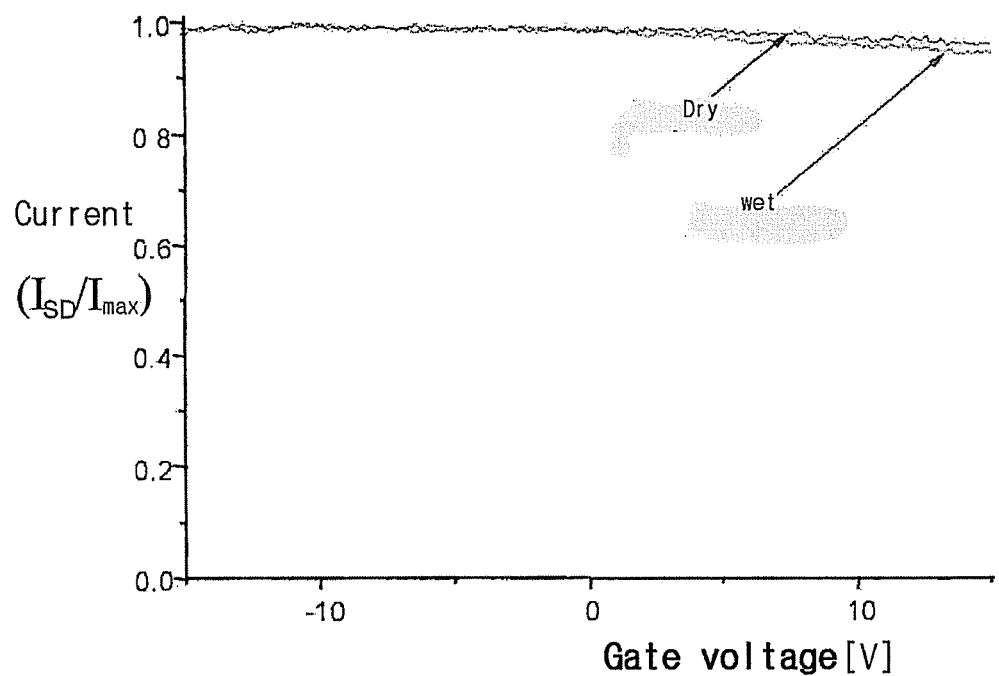
FIG. 7A shows that the reacted complex (i.e., SWCNT) is metallic since $I_{SD}$ (i.e., the current between the source and the drain) has constant value regardless of the gate voltage.
Figure 7B:
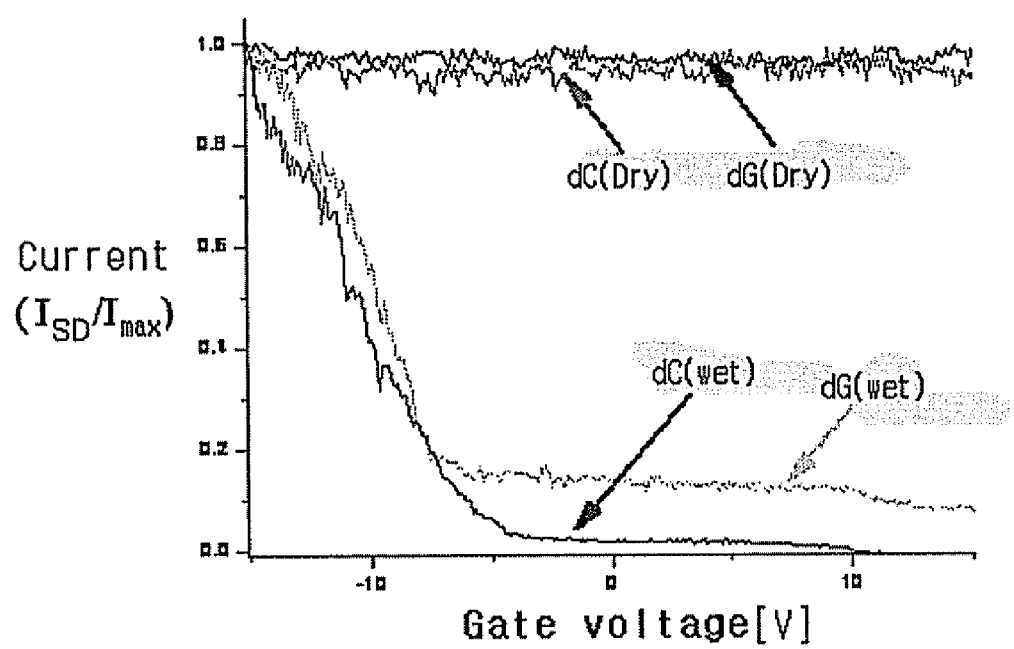
FIG. 7B shows that the SWCNT-DNA complex shows semi-conducting characteristics only when the complex is wet, thus it is important to measure the electrical characteristics of the complex in the solution.
Figure 7C:
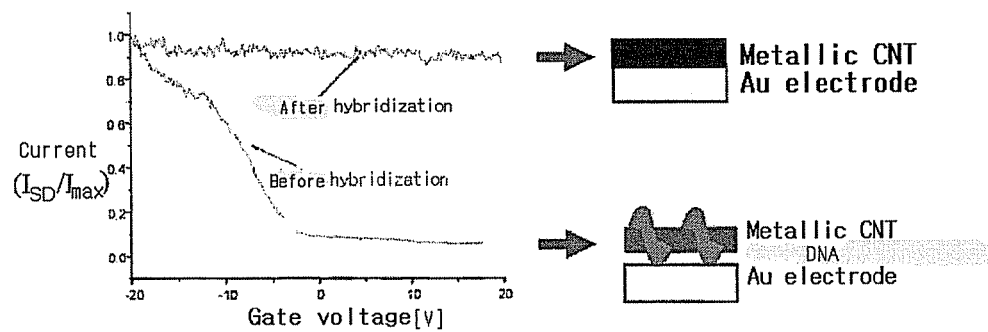
FIG. 7C shows that the reacted complex to target DNA is SWCNT and exhibits metallic behavior, whereas the unreacted complex exhibits semi-conducting behavior.

After SWCNTs or SWCNT-ssDNA complexes were positioned between the pair of electrodes of a device that generates a field effect, a current between a source and a drain was measured. Biomolecules to be measured and probes were implemented with (dG)18 and (dC)18 (see FIGS. 7A and 7B) or with 17 mer random base sequences (ccg acc gac gtc ggt cg) and their complementary strands (see FIG. 7C), respectively. In order to measure field effect, variations in current $I_{SD}$ between the source and the drain were measured with a semiconductor analyzer (HP4155A) by sweeping a gate voltage from −15 V to +15 V. The result is reported in FIGS. 7A to 7C. FIG. 7A shows that the assembled SWCNTs were metallic since $I_{SD}$ (i.e., a current flowing between the source and the drain) did not change according to a gate voltage irrespective of the existence of moisture when electric characteristics of the SWCNTs prior to reaction were measured. FIG. 7B shows the importance of maintaining a solution phase in a space between the pair of electrodes while the measurement was being carried out since the SWCNT-ssDNA complexes showed a semi-conducting property only in the solution phase. FIG. 7C is a graph illustrating that the CNTs were metallic when field effect was measured since probe ssDNAs were dissociated to reduce into the SWCNTs and that the complexes, which were not hybridized, were still SWCNT-ssDNA complexes.

As shown in FIG. 7A, when DNAs were combined with originally metallic SWCNTs, semi-conducting characteristics were obtained. Thus, when electric characteristics of reactants were measured after the complexes made of the metallic SWCNTs were reacted to the DNAs to be detected, metallic property indicates that the DNAs to be detected existed in a specification but semi-conducting property indicates that the DNAs to be detected did not exist in the sample.

Example 4

Figure 9A:
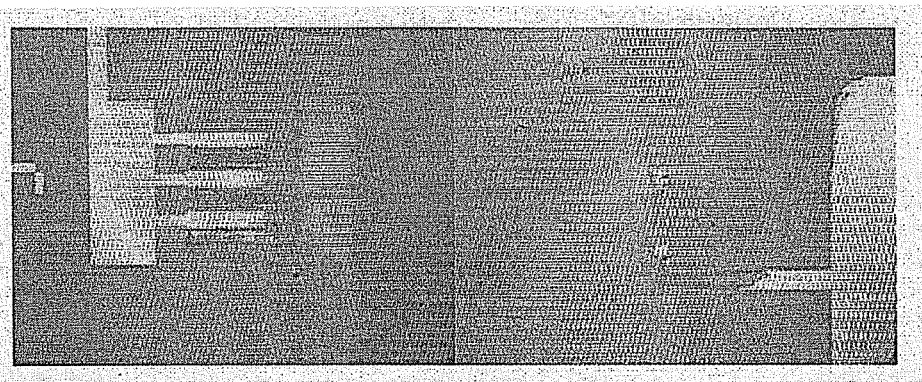
FIG. 9A is a picture showing damaged electrodes in the case of practicing a composite electric field-guided assembly in a buffer solution, where salts are dissolved, using an ordinary continuous DC electric field.

Assembling SWCNT-ssDNA Complexes in a Buffer Solution by Using a Pulsed Pseudo DC Electric Field According to the CEGA Method FIG. 9A is a picture showing damaged electrodes in the case of assembling SWCNT-ssDNA complexes in a buffer solution, where salts are dissolved, using an ordinary continuous DC electric field according to the CEGA method. Electrodes are damaged as shown in FIG. 9A since electrodes are oxidized due to the electrolysis when the continuous DC electric field is applied to the buffer solution wherein salts are dissolved.

Figure 9B:
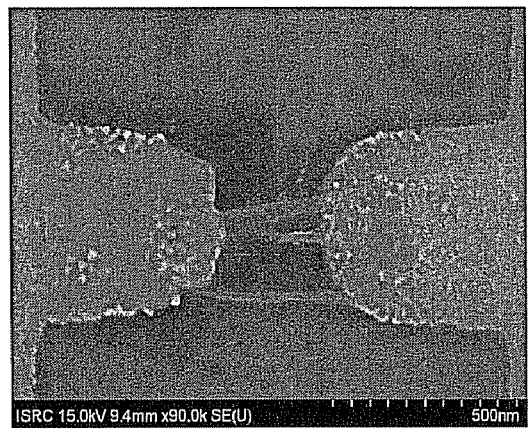
FIG. 9B is a picture showing SWCNT-ssDNA complexes assembled on the gap between the electrodes in a buffer solution, where salts are dissolved, using a pulsed pseudo DC electric field according to the composite electric field-guided assembly method.

FIG. 9B is a picture showing SWCNT-ssDNA complexes assembled well on the electrodes with a nano-sized gap in the case of assembling SWCNT-ssDNA complexes in a buffer solution, where salts are dissolved, using a pulsed pseudo DC electric field according to the CEGA method. Thus, it is preferable to position the SWCNT-ssDNA complexes or the SWCNTs on the gap between the pair of electrodes by using the pulsed pseudo DC electric field in a case where the SWCNT and ssDNAs are dissolved into the buffer solution that contains dissolved salts. In the composite electric field used to assemble SWCNT-ssDNA complexes, the frequency of the AC electric field (of sine wave) was 5 MHz, the intensity of the AC electric field was 2.96 $V_{peak}$, the frequency of the pseudo DC electric field of square wave was 500 kHz, and the intensity ratio of DC to AC electric field was 0.345. It took 1 minute to assemble SWCNT-ssDNA complexes.

Figure 9C:
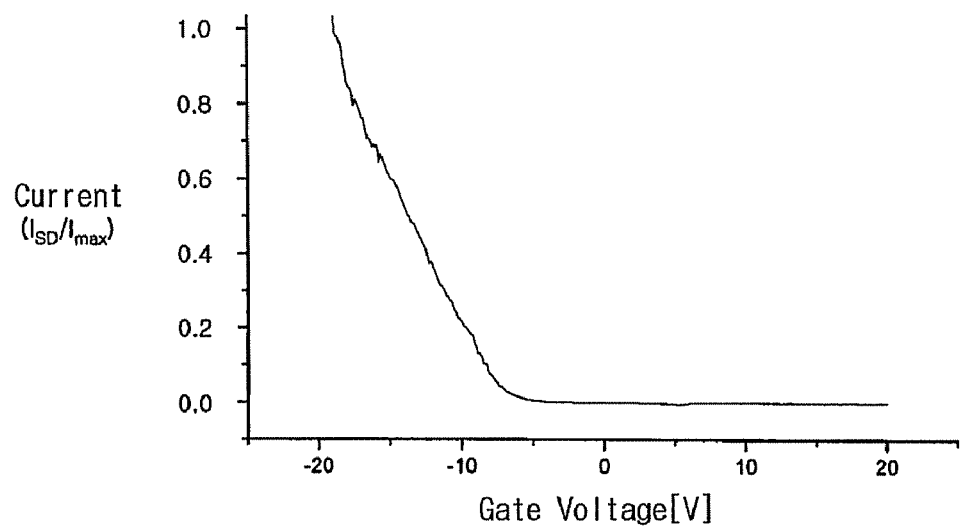
FIG. 9C is a graph showing the result of measuring the electrical characteristics of the SWCNT-ssDNA complexes from the device used in FIG. 9B.

FIG. 9C is a graph showing the result of measuring the electrical characteristics of the SWCNT-ssDNA complexes from the device used in FIG. 9B. As shown in FIG. 9C, the SWCNT-ssDNA complexes have semi-conducting characteristics and, it can be seen that the SWCNT-ssDNA complexes are assembled well in the gap between the pair of electrodes through the electrical characteristics.

While the aforementioned example has been described with respect to SWCNT and ssDNA, various complexes of nano elements and biomolecules can be adopted in the present invention.

The device and the method of detecting biomolecules as set forth above are a novel and new approach that can enhance reaction efficiency by fixing nano elements after reaction of nano elements in a solution phase as well as lower detection limit by using the CEGA method unlike conventional nano-bio sensors. Accordingly, it is possible to achieve an original technology that can cause innovation in the existing biosensor field in order to develop biosensors having enhanced characteristics such as detection density, time and volume. Furthermore, it is applicable to biosensor fields where it is desirable to measure a faint amount of biomolecules with high sensitivity as well as to high-tech detection methods such as a lab-on-a-chip method.

While the present invention has been described with reference to the particular illustrative embodiments and the accompanying drawings, it is not to be limited thereto but will be defined by the appended claims.

It is to be appreciated that those skilled in the art can substitute, change or modify the embodiments into various forms without departing from the scope and spirit of the present invention.

What is claimed is:

1. A device for electrical detection of biomolecules comprising:
    a substrate;
    a pair of electrodes on the substrate and having a gap therebetween;
    an electrode from which a voltage is applied between either one of the pair of electrodes, and the substrate;
    a detection solution comprising complexes including a carbon nanotube, and a probe which interacts with target biomolecules;
    a means for positioning the carbon nanotube in the detection solution on the gap between the pair of electrodes; and
    a means for measuring a change in electrical characteristics.

2. The device of claim 1, wherein the carbon nanotube is a metallic carbon nanotube.

3. The device of claim 2, wherein the carbon nanotube is a single-walled carbon nanotube.

4. The device of claim 1, wherein the target biomolecule is ribonucleic acid or deoxyribonucleic acid.

5. The device of claim 4, wherein the probe is a complementary ribonucleic acid or deoxyribonucleic acid to the target ribonucleic acid or deoxyribonucleic acid.

6. The device of claim 5, wherein the target biomolecule is a deoxyribonucleic acid, and the probe is a complementary single-stranded deoxyribonucleic acid to the target deoxyribonucleic acid.

7. The device of claim 1, wherein the positioning means is a DC power source device capable of applying a DC electric field between the electrodes and an AC power source device capable of applying an AC electric field between the electrodes.

8. The device of claim 7, wherein the DC electric field and the AC electric field are concurrently applied in the form of a composite electric field.

9. The device of claim 8, wherein the DC electric field is a continuously applied DC electric field or a non-continuously applied pseudo DC electric field.

10. The device of claim 1, wherein the measuring means of change in electrical characteristics is an ammeter to measure an electric current between the electrodes.

11. A method for fabricating a device for electrical detection of biomolecules comprising:
    mixing a carbon nanotube with a probe which interacts with target biomolecules, in a solution, thereby forming a detection solution that comprises a carbon nanotube-probe complex and/or carbon nanotubes;
    contacting the formed detection solution with a sample solution to form a mixture; the sample solution comprising biomolecules to be tested; and
    positioning the mixture of the detection solution and the sample solution in a gap between electrodes on a substrate;
    arranging the carbon nanotube-probe complex or the carbon nanotubes in the mixture in the gap between the electrodes, the arranging being accomplished by the application of a composite electric field; the composite electric field comprising an alternate current electric field and a direct current electric field that is in a continuous or non-continuous form.

12. A method for electrically detecting biomolecules, comprising:
    mixing a carbon nanotube with a probe which interacts with target biomolecules, in a solution; the interaction resulting in the formation of a detection solution that comprises a carbon nanotube-probe complex;
    contacting the formed detection solution with a sample solution to form a mixture; the sample solution comprising biomolecules to be tested;

positioning the mixture of the detection solution and the sample solution in a gap between electrodes on a substrate, thereby arranging the carbon nanotube-probe complex or the carbon nanotubes in the gap between the electrodes;

generating an electric field effect between the electrodes; and measuring a first electric field effect.

13. The method of claim 12, further comprising:

disposing the detection solution between the electrodes;

measuring a second electric field effect; and comparing the first electric field effect with the second electric field effect.

14. The method of claim 12, wherein the carbon nanotube is a metallic nanotube.

15. The method of claim 14, wherein the carbon nanotube is a single-walled carbon nanotube.

16. The method of claim 12, wherein the target biomolecule is a ribonucleic acid or deoxyribonucleic acid.

17. The method of claim 16, wherein the probe is a complementary ribonucleic acid or deoxyribonucleic acid to the target ribonucleic acid or deoxyribonucleic acid.

18. The method of claim 12, wherein the positioning occurs in the presence of a composite electric field; the composite electric field comprising a direct current electric field and an alternating current electric field.

19. The method of claim 18, wherein the direct current electric field is a non-continuously applied pseudo direct current electric field.

20. The method of claim 18, wherein the alternating current electric field of the composite electric field has an intensity ranging from 0.01 to 1000 $V_{peak}$, and a frequency ranging from a 1 MHz to a 10 GHz.

21. The method of claim 18, wherein the composite electric field has an intensity ratio of direct current electric field to the alternating current electric field less than or equal to about 1.

22. The method of claim 19, wherein the pseudo DC electric field has an intensity ratio less than or equal to about 1 relative to the AC electric field and a pulse frequency of the pseudo DC electric field ranging from about 1 KHz to about 10 Hz.

23. The method of claim 12, wherein the measurement of the electric field effect is carried out by using an ammeter to measure an electric current between the electrodes.

24. A method of positioning a carbon nanotube or a carbon nanotube-probe complex in a gap between electrodes, comprising:

disposing a solution comprising the carbon nanotube or the carbon nanotube-probe complex in the gap between the electrodes on a substrate; and arranging the carbon nanotube-probe complex or the carbon nanotube in the gap between the electrodes by applying a composite electric field; the composite electric field comprising an alternate current electric field and a direct current electric field.

25. The method of claim 24, wherein the direct current electric field is non-continuously applied.

* * * * *